(12) United States Patent
Hirono

(10) Patent No.: US 8,740,384 B2
(45) Date of Patent: Jun. 3, 2014

(54) METHOD AND APPARATUS FOR MEASURING MOLECULAR COMPOSITION

(75) Inventor: Taisuke Hirono, Hamamatsu (JP)

(73) Assignee: Kowa Company Ltd. (JP)

( * ) Notice: Subject to any disclaimer, the term of this patent is extended or adjusted under 35 U.S.C. 154(b) by 88 days.

(21) Appl. No.: 13/501,321

(22) PCT Filed: Sep. 22, 2010

(86) PCT No.: PCT/JP2010/066401
§ 371 (c)(1),
(2), (4) Date: Apr. 11, 2012

(87) PCT Pub. No.: WO2011/046005
PCT Pub. Date: Apr. 21, 2011

(65) Prior Publication Data
US 2012/0194785 A1    Aug. 2, 2012

(30) Foreign Application Priority Data
Oct. 14, 2009   (JP) ................................. 2009-236777

(51) Int. Cl.
*A61B 3/10*       (2006.01)
*A61B 3/00*       (2006.01)
*A61B 5/00*       (2006.01)

(52) U.S. Cl.
USPC ............ 351/221; 351/200; 351/205; 600/318

(58) Field of Classification Search
USPC .......... 351/200, 205, 221, 246; 600/300, 318, 600/322, 310, 473–477; 250/573–576
See application file for complete search history.

(56) References Cited

U.S. PATENT DOCUMENTS 5,258,788 A * 11/1993 Furuya ........................ 351/221
2005/0288564 A1* 12/2005 Iuliano ........................ 600/318

* cited by examiner

*Primary Examiner* — Dawayne A Pinkney
(74) *Attorney, Agent, or Firm* — Adams & Wilks

(57) ABSTRACT

A method and apparatus for measuring a molecular composition of protein molecules. A fluid containing at least two varieties of protein molecules is irradiated with first and second laser light beams having different wavelengths. The molecular composition of the at least two varieties of protein molecules contained in the fluid is measured on the basis of an autocorrelation function of a scattered light signal from the at least two varieties of protein molecules irradiated with the first and second laser light beams having different wavelengths.

19 Claims, 5 Drawing Sheets

METHOD AND APPARATUS FOR MEASURING MOLECULAR COMPOSITION

CROSS-REFERENCE TO RELATED APPLICATIONS

This application is a U.S. national stage application of International Application No. PCT/JP2010/066401 filed Sep. 22, 2010, claiming a priority date of Oct. 14, 2009, and published in a non-English language.

BACKGROUND OF THE INVENTION

1. Technical Field

The present invention relates to a method and apparatus for measuring a molecular composition, and relates more specifically to a method and apparatus for measuring a molecular composition in which a fluid containing at least two varieties of protein molecules is irradiated with a laser light beam, and scattered light is received from the protein molecules to measure their composition from a scattered light signal thereof.

2. Background Art

Aqueous humor flows in the anterior chamber disposed between the cornea and the crystalline lens of the eyeball. The albumin and other proteins in the aqueous humor are at a very low concentration in a normal eye due to the operation of the anterior chamber barrier. The aqueous humor also lacks blood cells.

However, it is known that when the function of the blood-aqueous barrier is reduced after intraocular lens insertion operations for cataracts or uveitis, white blood cells or red blood cells are discharged into the aqueous humor, the number of albumin molecules drastically increases, or globulin or the like that is a protein molecule larger than albumin is discharged.

Quantitatively measuring the number density of blood cells and the concentration of protein molecules is thus important for performing a follow-up diagnosis after surgery.

A method for calculating the protein concentration of the aqueous humor by irradiating the protein molecules suspended in the aqueous humor of the eyeball with laser light, and measuring the intensity of light scattered from the protein molecules is proposed as a method for quantitatively measuring the concentration of the protein molecules in the following Patent Document 1, for example.

The conventional technique described in Patent Document 1 concerns a measuring technique referred to as a laser flare-cell measuring technique using a single-wavelength laser, which provides information relating to the composition of proteins and various biomolecules contained in the aqueous humor inside of the anterior chamber of a human eye without contact and in a noninvasive manner.

PRIOR ART DOCUMENTS

Patent Documents

Patent Document 1: Japanese Laid-open Patent Publication No. 1992-352933

The protein contained in the aqueous humor is measured in order to measure the degree of inflammation in the anterior ocular segment, but conventional methods cannot measure whether the protein in the aqueous humor is the albumin present even in a healthy state, or the globulin is exuded when in a diseased state, or they cannot measure the albumin/globulin ratio (hereinafter referred to as the "A/G ratio"). In other words, conventional methods can quantitatively measure only the approximate degree of inflammation. This is due to the fact that the A/G ratio is reduced because the discharge of globulin molecules increases in a diseased state or in a state in which the blood-aqueous barrier is not fully functioning.

However, when the A/G ratio can be measured, the "quality" of the inflammation can be quantitatively measured and an appropriate treatment can be selected based on the inflammatory condition. In addition, the biological size can be detected by analyzing the fluctuation component of the scattered light, and identification can be made for components that have been indistinguishable as to whether it be albumin or prealbumin.

It is therefore an object of the present invention to provide a method and apparatus for measuring a molecular composition in which the composition or concentration of protein molecules in a sample or the aqueous humor of a human eye can be reliably measured without contact and in a non-invasive manner.

SUMMARY OF THE INVENTION

The present invention provides a method for measuring a molecular composition in which a fluid containing at least two varieties of protein molecules is irradiated with a laser light beam, and scattered light is received from the protein molecules to measure their composition from a scattered light signal thereof; the method comprising:

irradiating the protein molecules with a laser light beam having a predetermined wavelength;

irradiating the protein molecules with a laser light beam having a wavelength different from the predetermined wavelength; and measuring the composition of the protein molecules on the basis of an autocorrelation function of the scattered light signal from the protein molecules irradiated with the laser light beams having different wavelengths.

The present invention also provides an apparatus for measuring a molecular composition in which a fluid containing at least two varieties of protein molecules is irradiated with a laser light beam, and scattered light is received from the protein molecules to measure their composition from a scattered light signal thereof, the apparatus comprising:

a laser light source for emitting laser light beams having different wavelengths;

a correlator for determining an autocorrelation function of the scattered light signal from protein molecules irradiated with a laser light beam of a predetermined wavelength from the laser light source, as well as an autocorrelation function of the scattered light signal from protein molecules irradiated with a laser light beam having a wavelength different from the predetermined wavelength of the laser light beam; and a computer for computing the composition of the protein molecules on the basis of the autocorrelation functions determined based on the laser light beams having mutually different wavelengths.

In the present invention, the accuracy of identifying proteins is improved because protein molecules are irradiated with laser light beams having different wavelengths, and the composition of the protein molecules is measured from autocorrelation functions of a scattered light signal of the protein molecules. In addition, the ratio of albumin and globulin as protein molecules in the anterior chamber of a human eye can be measured without contact and in a noninvasive manner, contributing greatly to ophthalmologic diagnoses.

DETAILED DESCRIPTION OF THE INVENTION

Figure 1:
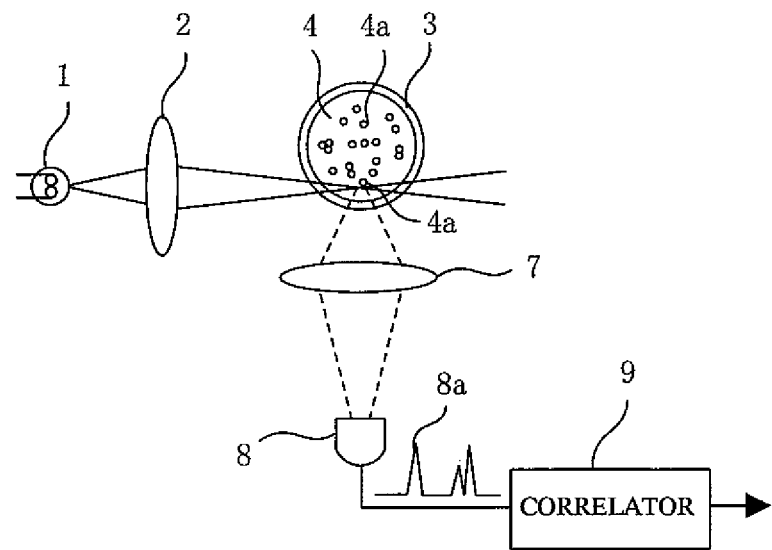
FIG. 1 is a view showing a configuration for determining an autocorrelation function of protein molecules in a sample.

The present invention will be described in detail hereinafter based on the embodiments shown in the drawings.

Embodiment 1

FIG. 1 shows the entire configuration of an apparatus for measuring a molecular composition according to one embodiment of the present invention. In this drawing, the reference numeral 1 indicates a light source, for example, a semiconductor laser light source. The laser light beam radiated from the semiconductor laser light source 1 is focused in a cylindrical glass sample cell (also referred to as a "cuvette") 3 by a lens 2. The light source is not limited to a semiconductor laser, and a He—Ne laser, a solid-state laser pumped by a semiconductor laser, a near infrared laser, or another laser light source may be used. In a case in which a near infrared laser is used, the laser may be used as an aiming beam having an optical path on which a visible light laser is superimposed.

Figure 2:
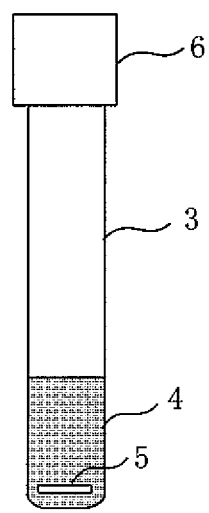
FIG. 2 is a front view of a sample cell.

As shown in FIG. 2, the sample cell 3 accommodates a magnetic stirrer bar (magnetic stirring bar) 5 as well as a sample 4 that contains particles such as protein molecules 4a. A cap 6 seals the sample cell 3. The magnetic stirrer bar 5 is caused to continuously stir the sample 4 into a uniform solution by a motor (not shown) disposed on the exterior.

The laser light beam from the semiconductor laser light source 1 is guided so as to pass through the sample cell 3 near the surface of an interior wall thereof, as shown in FIG. 1. Disposed perpendicularly to the interior wall thereof is a light receiving device including a lens 7 and a detector 8 composed of a photomultiplier or an APD (avalanche photodiode) photon counting module.

Laterally scattered light from the protein molecules 4a in the sample 4 that is irradiated with the laser light beam is incident on the detector 8 via the lens 7, and a scattered light signal 8a is output as a time series signal. The scattered light signal 8a is sent to a correlator 9 which performs autocorrelation analysis to determine the autocorrelation function of the scattered light.

Figure 3:
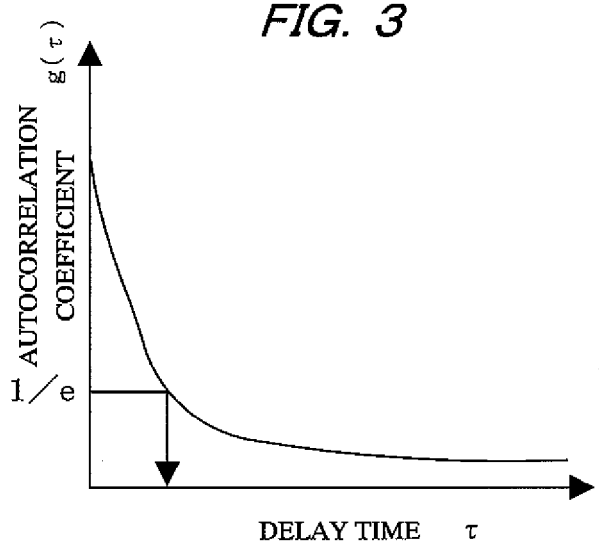
FIG. 3 is a graph showing an autocorrelation function determined using the configuration in FIG. 1.

A typical autocorrelation function obtained from the correlator 9 is shown in FIG. 3. Assuming that the value of the autocorrelation coefficient is 1 when the delay time $\tau$ is 0, the value $\tau_{1/e}$ of the delay time when the autocorrelation coefficient falls to 1/e is referred to as the relaxation coefficient, and it is a constant determined by the scattering material. Smaller molecules usually move faster, and the relaxation coefficient is therefore smaller (the autocorrelation function comes nearer to the left of the graph). Conversely, larger particles move slower, and the relaxation coefficient is therefore larger (coming nearer to the right of the graph).

Figure 4:
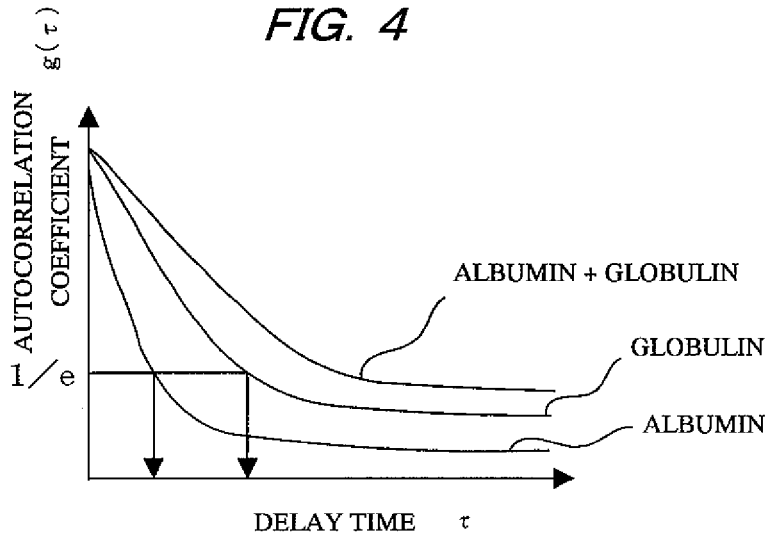
FIG. 4 is a graph showing an autocorrelation function of albumin, globulin, and a mixture system thereof.

FIG. 4 shows an autocorrelation function obtained from the correlator 9 in a case in which albumin, globulin, or albumin and globulin are contained in the sample 4 in a predetermined ratio. It is known that the molecular size of albumin is small, about 8 nm, and the molecular size of globulin is larger, distributed over a wide range of about 10 to 100 nm, yielding measurement results such as those shown in FIG. 4. However, in a case in which measurements are taken of a mixture system of albumin and globulin in a predetermined proportion, overlapping takes place, and the autocorrelation function shown at the top in FIG. 4 is measured.

The square root of the autocorrelation coefficient $G_1(\tau)$ of the mixture system is expressed as the below-described Mathematical Formula 1, where $\lambda_1$ is the wavelength of the semiconductor laser light source 1.

$$\lambda_1 \rightarrow \sqrt{G_1(\tau)} = \sqrt{AT<N>^2}|S_1 C_1 e^{-\Gamma_1 \tau} + S_2 C_2 e^{-\Gamma_2 \tau}| \quad \text{[Mathematical Formula 1]}$$

Here, A is the degree of coherence, T is the measurement time, N is the number of photons detected by the detector 8, $S_1$ is the scattering efficiency of albumin, $C_1$ is the albumin concentration, $\Gamma_1$ is the relaxation coefficient of albumin, $S_2$ is the scattering coefficient of globulin, $C_2$ is the globulin concentration, and $\Gamma_2$ is the relaxation coefficient of globulin.

Figure 7:
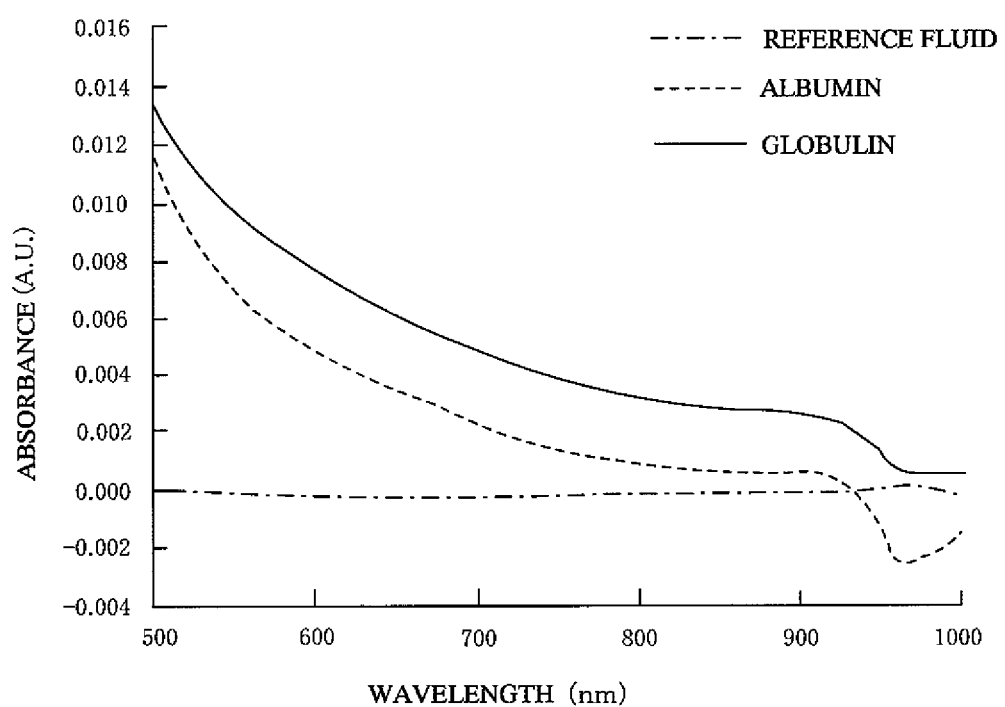
FIG. 7 is a graph showing the wavelength dependence of the absorbance of albumin and globulin.

The fact that the scattering efficiency and the relaxation coefficient have wavelength dependence is used in order to calculate the albumin and globulin concentrations, or the ratio thereof from the autocorrelation function of the mixture system. For example, the relaxation coefficient of the autocorrelation coefficient decreases when the wavelength of the light source increases. The scattering efficiency also exhibits wavelength dependence such as shown in FIG. 7. In FIG. 7, the vertical axis is the absorbance (A.U.; arbitrary units), and the total value of the scattering efficiency and the absorbance is 1. The dot-dashed line, dotted line, and solid line in FIG. 7 indicate the absorbance of a reference fluid, albumin, and globulin, respectively.

Figure 5:
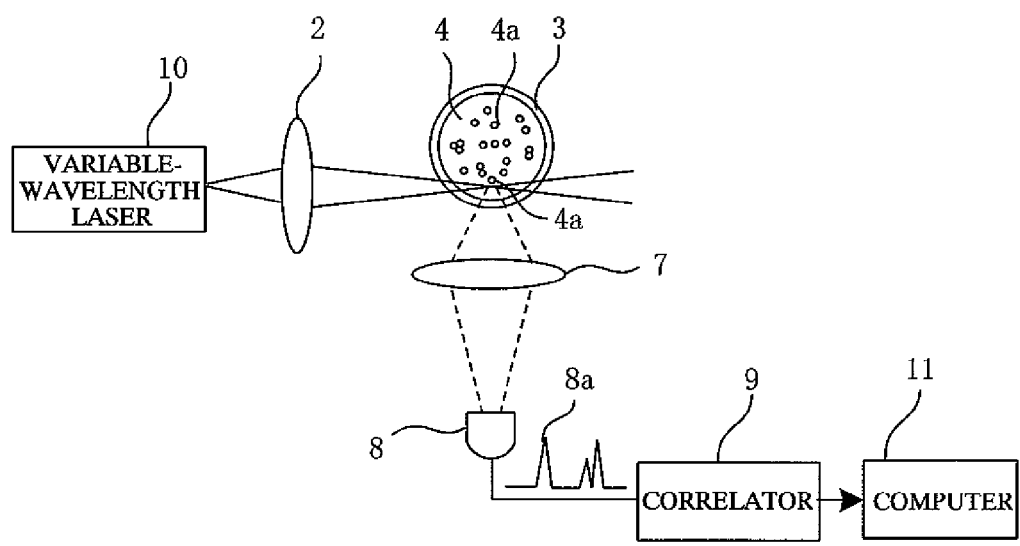
FIG. 5 is a view showing a configuration of an apparatus for measuring the composition of protein molecules in a sample cell.

In view of this, a variable-wavelength laser light source 10 is used as the light source, as shown in FIG. 5, and the autocorrelation function of the mixture system is measured. The light source in this case may also be a swept-wavelength laser, or a laser employing a diffraction grating or a filter tunable to white light. The configuration in FIG. 5 is the same as in FIG. 1 except that the variable-wavelength laser light source 10 is used as the light source, and a computer 11 for computing the albumin and globulin concentrations is connected to the rear of the correlator 9. Descriptions of identical sections are therefore omitted.

It is now assumed that $\lambda_1$ (for example, $\lambda_1=700$ nm) is the wavelength of the laser light beam emitted from the variable-wavelength laser light source 10. The correlator 9 then calculates the autocorrelation coefficient $G_1(\tau)$ and the computer 11 computes the square root of the autocorrelation coefficient $G_1(\tau)$ shown in Mathematical Formula 1, whose value is stored in the memory (not shown) in the computer 11.

Next, the wavelength of the laser light beam emitted from the variable-wavelength laser light source 10 is varied from $\lambda_1$ to $\lambda_2$ (for example, $\lambda_2=960$ nm). The degree of coherence A, the number of photons N, the scattering efficiencies $S_1$, $S_2$ of albumin and globulin, and the relaxation coefficients $\Gamma_1$, $\Gamma_2$ of albumin and globulin are then changed to A', N', $S'_1$, $s'_2$, $\Gamma'_1$, and $\Gamma'_2$, respectively, and the square root of the autocorrelation coefficient $G_2(\tau)$ calculated by the correlator 9 is computed by the computer 11 in accordance with the following Mathematical Formula 2. The computed value is then stored in the memory of the computer 11.

$$\lambda_2 \rightarrow \sqrt{G_2(\tau)} = \sqrt{A'T<N'>^2}|S_1'C_1 e^{-\Gamma'_1 \tau} + S_2'C_2 e^{-\Gamma'_2 \tau}| \quad \text{[Mathematical Formula 2]}$$

Simplifying Mathematical Formulas 1 and 2 results in Mathematical Formulas 3 and 4, respectively. Each of the values is stored in the memory in the same manner.

$$\sqrt{G_1(\tau)} \cong \alpha C_1 + \beta C_2 \quad \text{[Mathematical Formula 3]}$$

$$\sqrt{G_2(\tau)} \cong \alpha' C_1 + \beta' C_2 \quad \text{[Mathematical Formula 4]}$$

Here, $\alpha$ is the constant determined by A, T, N, $S_1$, $\Gamma_1$, and $\tau$ when the wavelength is $\lambda_1$; $\beta$ is the constant determined by A, T, N, $S_2$, $\Gamma_2$, and $\tau$ when the wavelength is $\lambda_1$; $\alpha'$ is the constant determined by A', T', N', $S'_1$, $\Gamma'_1$, and $\tau$ when the wavelength is $\lambda_2$; and $\beta'$ is the constant determined by A', T', N', $S'_2$, $\Gamma'_2$, and $\tau$ when the wavelength is $\lambda_2$.

The concentrations $C_1$, $C_2$ of albumin and globulin are then calculated as shown in the below-described Mathematical Formula 5 from Mathematical Formulas 3 and 4 stored in the memory of the computer 11.

$$C_1 = \frac{\beta'\sqrt{G_1(\tau)} - \beta\sqrt{G_2(\tau)}}{\alpha\beta' - \alpha'\beta} \quad \text{[Mathematical Formula 5]}$$

$$C_2 = \frac{\alpha'\sqrt{G_1(\tau)} - \alpha\sqrt{G_2(\tau)}}{\alpha'\beta - \alpha\beta'}$$

The concentrations of albumin and globulin suspended in the sample can thus be calculated by changing the wavelength of the laser light beam radiated on the protein molecules in the sample. The ratio $C_1/C_2$, that is, A/G, can also be calculated from the concentrations $C_1$, $C_2$.

Embodiment 2

The composition (concentration) of the protein molecules 4a of albumin and globulin contained in the sample 4 inside of the sample cell 3, or the ratio thereof, was calculated in the aforedescribed Example 1. On the other hand, the composition (concentration) of the protein molecules 4a of albumin and globulin suspended in the aqueous humor in an anterior chamber 21 of a human eye (eye under test) 20, or the ratio thereof, is calculated in the embodiment shown in FIG. 6.

The only difference in comparison with the embodiment shown in FIG. 5 is that the sample cell 3 has been replaced with the anterior chamber 21 of the human eye 20. The wavelength of the laser light beam from the variable-wavelength laser light source 10 is set to $\lambda_1$, and the beam is passed through the eye near the anterior chamber 21. The laterally scattered light from the protein molecules 4a suspended in the aqueous humor inside of the anterior chamber 21 that is irradiated with the laser light beam having a wavelength $\lambda_1$ is incident on the detector 8 via the lens 7, and the scattered light signal 8a is output as a time series signal. The scattered light signal 8a is sent to the correlator 9 for performing autocorrelation analysis, and the square root of the autocorrelation coefficient shown in Mathematical Formula 1 is computed by the computer 11 and stored in the memory.

Next, the wavelength of the laser light beam emitted from the variable-wavelength laser light source 10 is changed to $\lambda_2$, the square root of the autocorrelation coefficient $G_2(\tau)$ calculated by the correlator 9 is computed at this time in accordance with Mathematical Formula 2, and the resulting value is stored in the memory of the computer 11. The concentrations $C_1$, $C_2$ of albumin and globulin in the anterior chamber 21, or the ratio thereof, are then computed in accordance with Mathematical Formulas 3 to 5.

Figure 6:
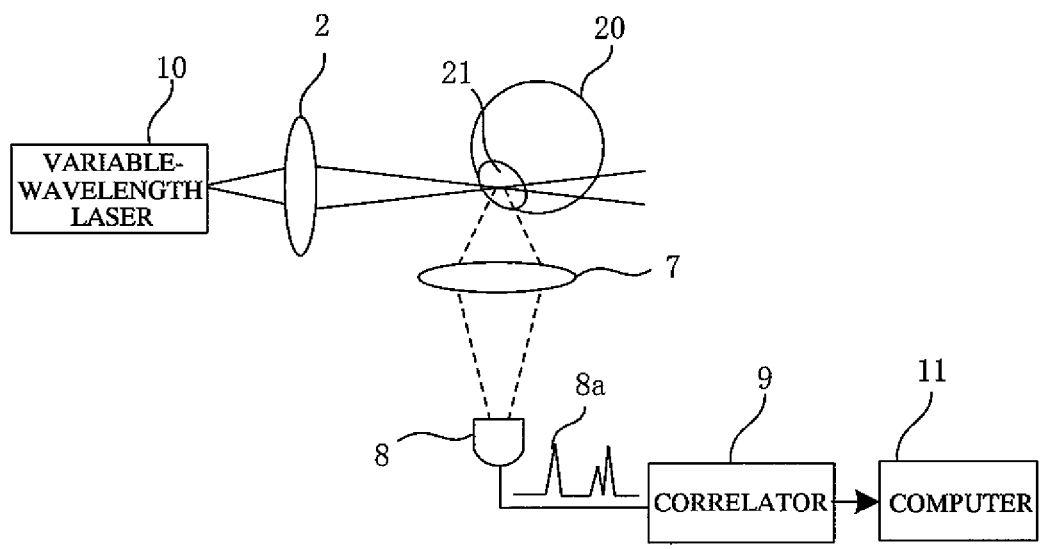
FIG. 6 is a view showing a configuration of an apparatus for measuring the composition of protein molecules in an aqueous humor of a human eye.

The variable-wavelength laser light source 10 is used in order to change the wavelength of the laser light beam in the embodiments in FIGS. 5 and 6, but the wavelength of the laser light beam may be changed by providing two laser light sources having different wavelengths and switching these laser light sources.

The computer 11 is provided separate from the correlator 9 in the aforedescribed Embodiments 1 and 2, but the correlator 9 may perform computing by the computer 11.

In addition, the composition (concentration) of the protein molecules of albumin and globulin, or the ratio thereof, is calculated in the aforedescribed Embodiments 1 and 2, but the composition of other protein molecules, biomolecules, or particulates may also be calculated which have a wavelength dependence at least in the scattering efficiency and/or relaxation coefficient when the autocorrelation function is calculated.

| | Key to the Symbols |
|---|---|
| 1 | Semiconductor laser light source |
| 3 | Sample cell |
| 4 | Sample |
| 4a | Protein molecule |
| 8 | Detector |
| 9 | Correlator |
| 10 | Variable-wavelength laser light source |
| 11 | Computer |
| 20 | Human eye |
| 21 | anterior chamber |

The invention claimed is:

1. A method for measuring a molecular composition of protein molecules, comprising:
   irradiating a fluid containing at least two varieties of protein molecules with a first laser light beam having a predetermined wavelength;
   irradiating the fluid containing the at least two varieties of protein molecules with a second laser light beam having a wavelength different from the predetermined wavelength; and
   measuring the molecular composition of the at least two varieties of protein molecules contained in the fluid on the basis of an autocorrelation function of a scattered light signal from the at least two varieties of protein molecules irradiated with the first and second laser light beams having different wavelengths.

2. A method for measuring a molecular composition according to claim 1; wherein the at least two varieties of protein molecules are protein molecules suspended in an aqueous humor inside of an anterior chamber of a human eye.

3. A method for measuring a molecular composition according to claim 1; wherein the at least two varieties of protein molecules are protein molecules suspended in a solution inside of a sample cell.

4. A method for measuring a molecular composition according to claim 1; wherein the step of measuring the molecular composition comprises measuring the concentration or ratio of the at least two varieties of protein molecules.

5. A method for measuring a molecular composition according to claim 4; wherein the at least two varieties of protein molecules are albumin and globulin.

6. A method for measuring a molecular composition according to claim 1; wherein the at least two varieties of protein molecules are albumin and globulin.

7. An apparatus for measuring a molecular composition of protein molecules, the apparatus comprising:
   a laser light source for irradiating a fluid containing at least two varieties of protein molecules with a first laser beam having a predetermined wavelength and for irradiating the fluid containing the at least two varieties of protein molecules with a second laser light beam having a wavelength different from the predetermined wavelength;

a correlator for determining a first autocorrelation function of a scattered light signal from the at least two varieties of protein molecules irradiated with the first laser light beam by the laser light source, and for determining a second autocorrelation function of a scattered light signal from the at least two varieties of protein molecules irradiated with the second laser light beam by the laser light source; and a computer for computing the composition of the at least two varieties of protein molecules on the basis of the first and second autocorrelation functions determined by the correlator.

8. An apparatus for measuring a molecular composition according to claim 7; wherein the at least two varieties of protein molecules are protein molecules suspended in an aqueous humor inside of an anterior chamber of a human eye.

9. An apparatus for measuring a molecular composition according to claim 7; wherein the at least two varieties of protein molecules are protein molecules suspended in a solution inside of a sample cell.

10. An apparatus for measuring a molecular composition according to claim 7; wherein the computation by the computer of the composition of the at least two varieties of protein molecules comprises the measurement of the concentration or ratio of the at least two varieties of protein molecules.

11. An apparatus for measuring a molecular composition according to claim 10; wherein the at least two varieties of protein molecules are albumin and globulin.

12. An apparatus for measuring a molecular composition according to claim 7; wherein the at least two varieties of protein molecules are albumin and globulin.

13. A method of non-invasively measuring a molecular composition of protein molecules, comprising:
irradiating protein molecules with laser beams having different wavelengths;
determining autocorrelation functions of scattered light signals of the protein molecules irradiated with the laser beams having different wavelengths; and
measuring the molecular composition of the protein molecules on the basis of the determined autocorrelation functions.

14. A method for measuring a molecular composition according to claim 13; wherein the step of measuring the molecular composition comprises measuring the concentration or ratio of the protein molecules.

15. A method for measuring a molecular composition according to claim 14; wherein the protein molecules comprise albumin and globulin.

16. A method for measuring a molecular composition according to claim 13; wherein the protein molecules comprise albumin and globulin.

17. A method according to claim 13;
wherein the protein molecules are suspended in an aqueous humor inside of an anterior chamber of a human eye.

18. A method according to claim 17;
wherein the protein molecules comprise albumin and globulin.

19. A method according to claim 13;
wherein the protein molecules are suspended in a solution inside of a sample cell.

* * * * *